United States Patent [19]
DeCote, Jr.

[11] Patent Number: 4,462,406
[45] Date of Patent: Jul. 31, 1984

[54] DUAL CHANNEL ISOLATION SYSTEM FOR CARDIAC PACER

[75] Inventor: Robert DeCote, Jr., Miami Beach, Fla.

[73] Assignee: Cordis Corporation, Miami, Fla.

[21] Appl. No.: 375,039

[22] Filed: May 5, 1982

[51] Int. Cl.³ .............................................. A61N 1/36
[52] U.S. Cl. ............................................. 128/419 PG
[58] Field of Search ................................ 128/419 PG

[56] References Cited
U.S. PATENT DOCUMENTS

| | | | |
|---|---|---|---|
| 3,135,264 | 6/1964 | Tischler et al. | 128/423 |
| 3,669,120 | 6/1972 | Nielsen | 128/419 PG |
| 3,773,033 | 11/1973 | Robkard et al. | 128/700 |
| 3,815,109 | 6/1974 | Carraway et al. | 128/903 |
| 3,903,897 | 9/1975 | Woollons et al. | 128/419 PG |
| 4,248,238 | 2/1981 | Joseph | 128/419 PG |
| 4,266,551 | 5/1981 | Stein | 128/419 PG |
| 4,300,566 | 11/1981 | Stindt et al. | 128/419 PG |

Primary Examiner—William E. Kamm
Assistant Examiner—Mitchell J. Shein
Attorney, Agent, or Firm—Kenway & Jenney

[57] ABSTRACT

To prevent crosstalk between atrial and ventricular channels in a dual chamber cardiac pacer with bipolar leads, the atrial and ventricular leads are multiplexed at about 2 kHz. This chopping rate is well above the sense amplifier's upper frequency response.

Solid state switches provide that during stimulation on a given channel, only the corresponding leads are connected. Between output pulses, only one of the bipolar lead pairs is connected to the pacer at any instant of time. Circuitry is included to provide break-before-make action. Thus, at no instant of time are both channel lead pairs connected to the pacer.

9 Claims, 6 Drawing Figures

DUAL CHANNEL ISOLATION SYSTEM FOR CARDIAC PACER

BACKGROUND OF THE IVENTION

The invention relates generally to cardiac pacers, and more particularly to means for preventing crosstalk between bipolar pacer leads.

There are two major pumping chambers in the heart, the left and right ventricles. Simultaneously contracting, these chambers expel blood into the aorta and the pulmonary artery. Blood enters the ventricles from the left and right atria, respectively. The atria contract in a separate action which precedes the major ventricular contraction by an interval of about 100 milliseconds (ms), known as the AV delay. The contractions arise from a wave of electrical excitation which begins in the right atrium and spreads to the left atrium. The excitation then enters the atrio-ventricular (AV) node which delays its passage via the bundle of His into the ventricles. Atrial contractions begin every 400–1,000 ms at a metabolically determined frequency known as the "sinus" rate.

Electrical signals corresponding to the contractions appear in the electrocardiagram. A signal known as the P-wave accompanies atrial contraction while a signal known as the QRS complex, with a predominant R-wave, accompanies the ventricular contraction.

The typical implanted cardiac pacer operates by supplying missing stimulation pulses to provide excitation via an insulated wire (or "pacing lead") terminating in an electrode attached to the right ventricle. The naturally occurring R-wave can be reliably detected by the same lead to inhibit or trigger stimulation or to restart a timing interval as in "demand" pacing. An additional pacer lead contacts the atrium to sense P-waves, if desired. Pacers whose ventricular stimulation is timed from the sensing of a P-wave are referred to as AV synchronous or "physiological" pacers since they preserve the natural sinus rate as well as the normal sequence of contractions. In AV sequential pacers, the atrial lead is used for atrial stimulation. Examples of physiological AV sequential pacers or "double demand" pacers in which the atrial and ventricular leads can both stimulate and sense are shown in pending U.S. patent application Ser. No. 153,422 entitled "Ventricular Inhibited Cardiac Pacer" filed May 27, 1980 and U.S. patent application Ser. No. 207,003 entitled "Multi-Mode Microprocessor Based Programmable Cardiac Pacer" filed Nov. 14, 1980, both assigned to the assignee of the present application, and incorporated herein by reference in their entirety.

There are two types of electrode systems used in pacing leads. Unipolar leads terminate distally in a single electrode (cathode) and employ the case of the pulse generator itself, or a conductive plate on the case, as the return electrode or ground (anode). Bipolar pacing leads, on the other hand, teminate distally in two spaced insulated electrodes connected to the pulse generator through respective wires in the pacing lead. Thus, each bipolar lead carries a positive and negative electrode for the respective chamber, and the case is not designed to form a part of the electrical circuit in this configuration. The two positive electrodes on the respective bipolar leads are tied together electrically through a common ground connection.

In an AV sequential bipolar lead pacing system, this shared ground connection can present crosstalk problems in both sensing and stimulation when each bipolar lead is in a different heart chamber. This is an extremely important problem to solve for physiological pacers which provide bipolar stimulation and sensing for both heart chambers wth the same pacer powered by a single battery.

One of the ways previously used to accomplish some measure of isolation between bipolar leads is to employ a transformer in the output stage of the pacing circuit to isolate the lead electrodes. This approach, however, has the serious drawback of allowing pacing isolation, but not allowing sensing isolation. In addition, it necessitates adding a relatively bulky, inefficient and noise susceptable component to the otherwise miniaturized pacer electronics.

SUMMARY OF THE INVENTION

The general object of the invention is to virtually eliminate all crosstalk between ventricular and atrial channels in a dual chamber cardiac pacer. Such isolation improves the pacer's ability to reliably detect characteristic features of electrical waveforms appearing on the pacing leads and insures delivery of stimulation energy to the desired heart chamber. This objective is accomplished by quiescently multiplexing the atrial and ventricular channels at a rate of about 2 KHz in the absence of pacer stimulation pulses. An oscillator produces a clock signal which toggles a set of semiconductor switches in a break-before-make fashion. The switches alternately connect the pulse generator's atrial and ground terminals to the atrial lead, and the ventricular and ground terminals to the ventricular lead. This system completely avoids the common ground connection between the channels, thus reducing the possibility of crosstalk and cross-stimulation. When the pacer issues a stimulation pulse for a given channel, the other channel is automatically disconnected while the one channel is connected for a predetermined fixed interval covering the maximum pulse width. Multiplexing continues immediately following the fixed interval. Thus, in either stimulating or sensing modes, the channel connections are mutually exclusive.

DESCRIPTION OF THE PREFERRED EMBODIMENT

Figure 1:
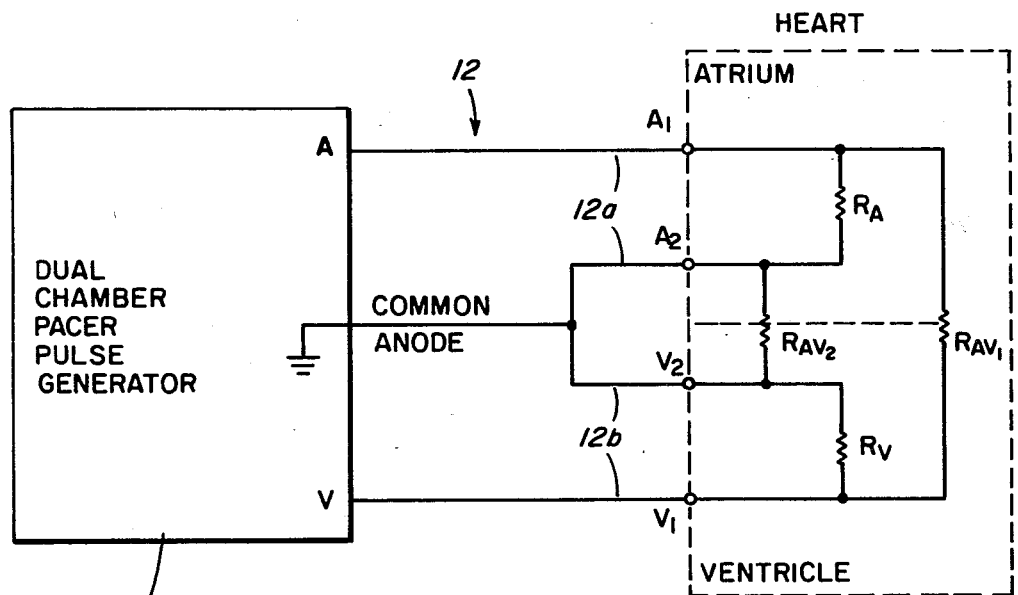
FIG. 1 is a schematic representation of the prior art dual chamber bipolar pacing system.

FIG. 1 illustrates the nature of the crosstalk problem inherent in prior art dual chamber bipolar lead pacing systems. A cardiac pacer pulse generator 10 contains the pacing logic circuitry sealed together with the battery cells in the customary biologically campatible hermetic enclosure. The pacer pulse generator 10 is implanted at a suitable location in the body, such as the axillary region, and is electrically interconnected with a three conductor pervenous pacer lead 12 which terminates in an atrial lead 12a having spaced electrodes A1 (tip) and A2 (ring) in electrical contact with the inside of the right atrium of the heart. The ventricular branch 12b of the pacer lead terminates in spaced electrodes V1 (tip) and V2 (ring) located inside the right ventricle. Electrodes A1,A2, V1 and V2 have characteristic inter-electrode resistances through electrically conductive pathways in the heart. Characteristic resistances $R_A$ and $R_V$ appear between the atrial and ventricular electrodes respectively while the inter-electrode resistance between electrodes A1 and V1 is $R_{AV1}$. Because electrodes A2 and V2 share a common ground connection (anode), they are at the same reference potential in FIG. 1. Note that these electrodes short circuit some myocardial tissue, represented by $R_{AV2}$, like a "staple" in the heart.

When the pacer 10 applies an output pulse to the ventricular chamber via lead 12b, a portion of the electrical current can return to anode via the inter-chamber resistance $R_{AV1}+R_A$ (typically on the order of 2 kilohms) to atrial anode A2 as well as to the intended ventricular anode V2. This unintended spill-over of stimulation pulse energy to the other chamber could cause a spurious atrial contraction or destabilization in addition to the intended ventricular contraction. This is referred to as cross-stimulation. Similarly, signals originating in the cardiac muscle in the form of R or P-waves are disrupted by the A2—V2 connection and can be conducted via the heart resistance $R_{AV1}$ such that an attenuated version appears simultaneously on the other channel. This is referred to as cross-sensing.

Figure 2:
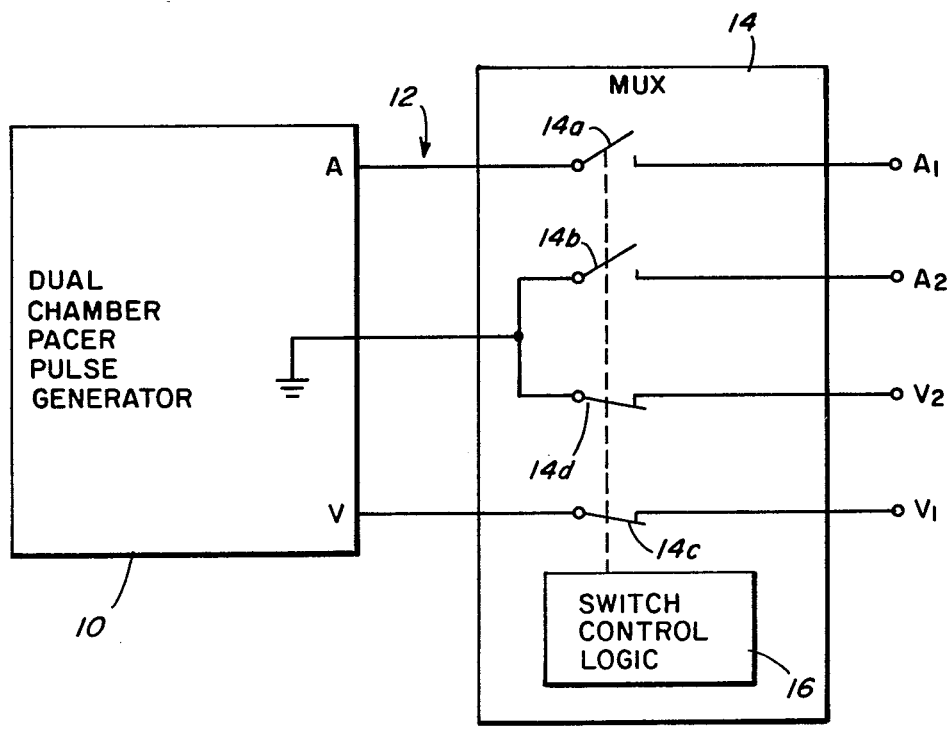
FIG. 2 is a schematic representation of the channel isolation system according to the present invention.

A solution to these problem is illustrated in FIG. 2. Without altering the pacing logic or output circuitry of the dual chamber pacer 10, the system of FIG. 2 insures a high degree of isolation between atrial and ventricular channels by time-sharing their connection to the pacer 10 via a multiplexor circuit 14. The atrial terminals A1 and A2 are connected to the atrial and ground terminal of pulse generator 10 via respective electronic switch pair 14a and 14b. Similarly the ventricular electrodes are connected to the ventricular and ground terminal of the pulse generator 10 via switch pair 14c and 14d respectively. when atrial switch pair 14a and 14b are both open, ventricular pair 14c and 14d are both closed, and vice-versa, as determined by switch control logic 16. In the absence of an output stimulation pulse from pacer 10 (the quiescent state), switch control logic 16 alternately toggles both switch pairs at a frequency which is high compared with the cardiac waveforms which are to be detected by the sense amplifier of the pacer 10. When a pacer stimulation pulse occurs, the switch control logic 16 is designed to hold the appropriate switch pair closed (and the other pair open) until after the stimulation pulse, and then resume channel alternation.

Figure 3:
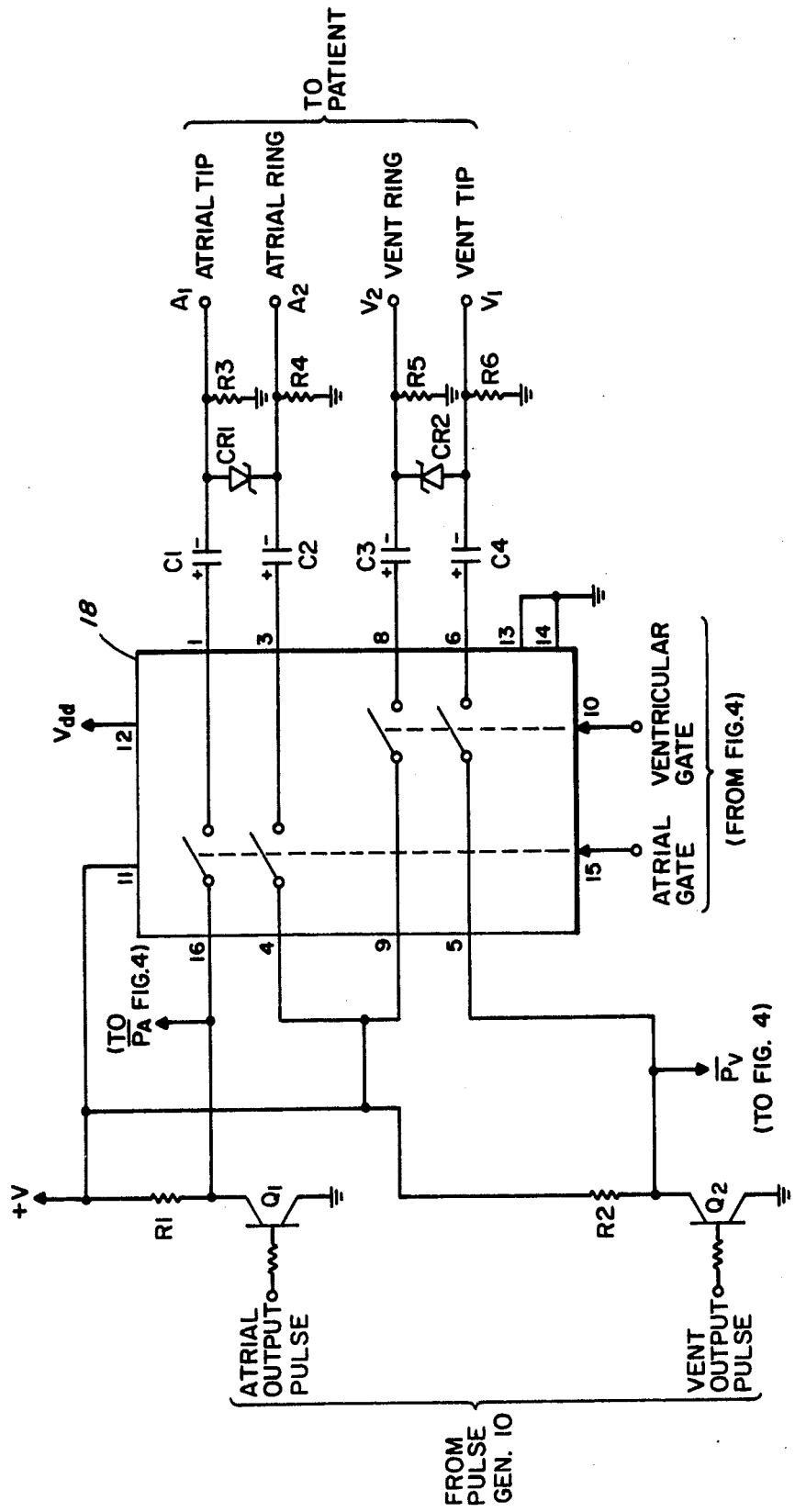
FIG. 3 is a detailed schematic diagram of the multiplexing system according to the present invention.
Figure 4:
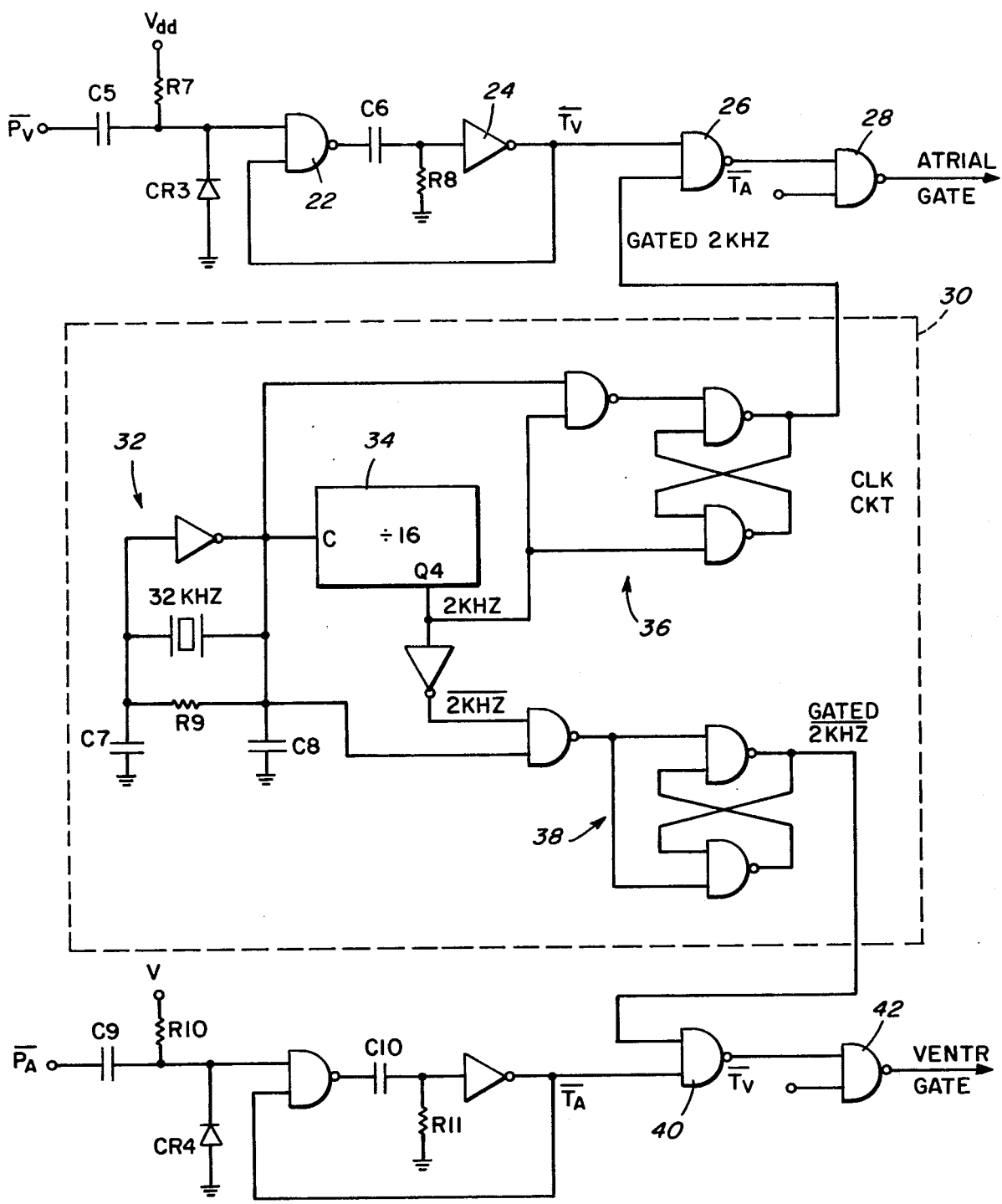
FIG. 4 is a schematic drawing of the gating circuitry associated with the multiplexing circuitry of FIG. 3.

FIGS. 3, and 4 illustrate an embodiment of the multiplexing system of FIG. 2. The atrial and ventricular terminals as well as the anode of the pulse generator 10 are connected as shown in FIG. 3 to a quad analog switch circuit 18. The four independently operable electronic switches in the analog switch circuit 18 correspond to switches 14a through 14d of FIG. 2. However, the atrial and ventricular switch pairs are connected for tandom operation by separate atrial and ventricular gate signals respectively produced by the gating circuit shown in FIG. 4.

Figure 6:
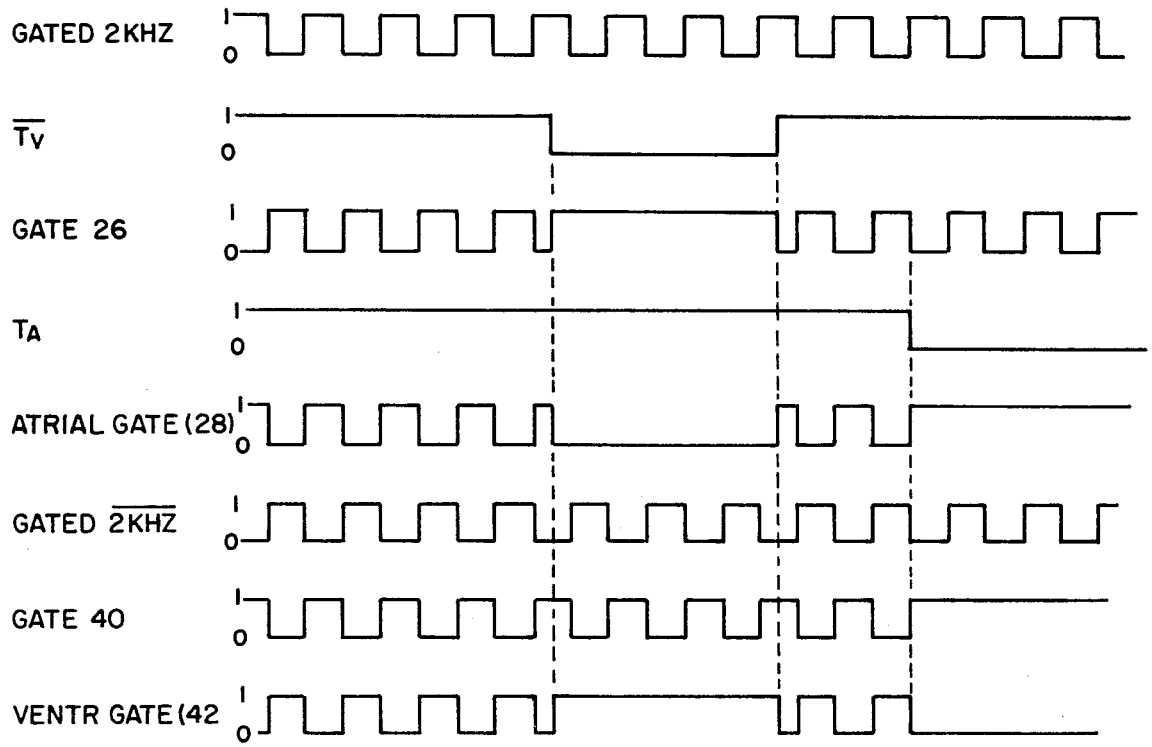
FIG. 6 is a timing diagram of signals in the gating circuitry of FIG. 4 in the presence of stimulation pulses.

When the pulse generator 10 produces a ventricular output pulse, complementary signal $P_V$-bar (i.e., the collector of transistor Q2 in FIG. 3) goes low. Capacitor C5 (FIG. 4) differentiates this signal causing a momentary zero input to NAND gate 22. The impressed charge on capacitor C6 holds the output of inverter 24 low until discharged through resistor R8 below the zero threshold of inverter 24, at which point the output of NAND gate 22 regeneratively returns low. Thus in the absence of a ventricular output stimulation pulse, signal $T_V$-bar (FIG. 4) is quiescently high as shown in FIG. 6. The circuit producing $T_V$-bar operates as a non-retriggerable one-shot. The one-shot period is arranged to be a bit longer than the longest pacer pulse width. The circuit producing signal $T_A$-bar operates similarly, but in response to atrial stimulation output pulses from the pacer 10. Thus signal $T_A$-bar is also quiescently high in the absence of a stimulation pulse.

Figure 5:
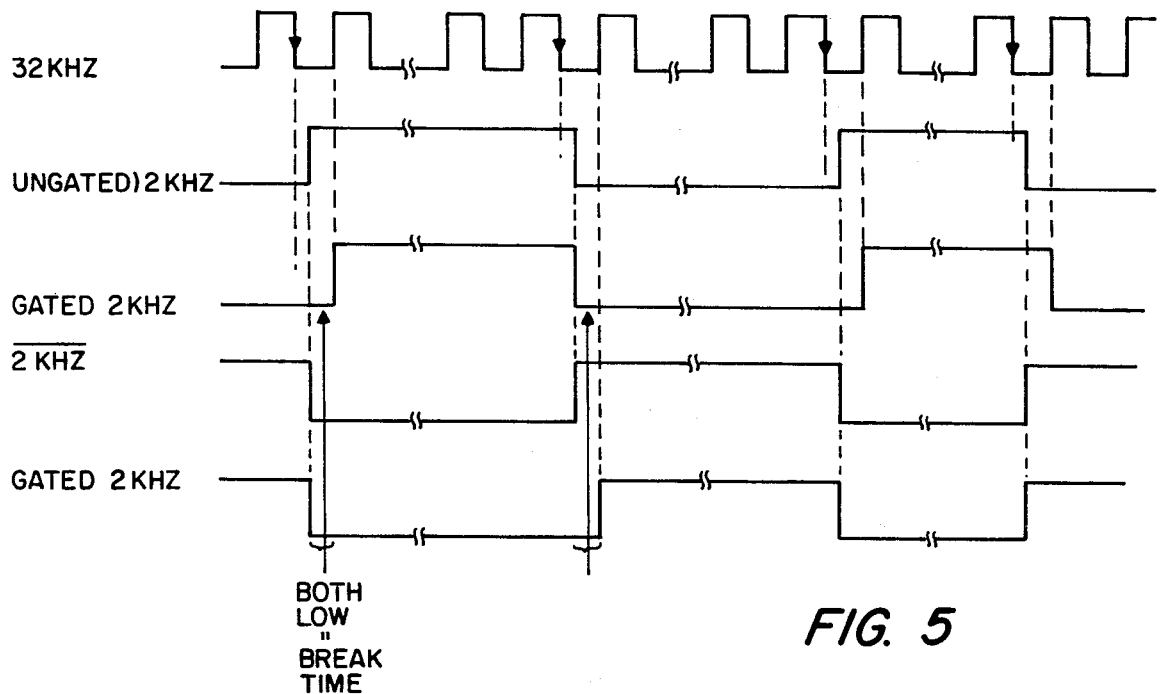
FIG. 5 is a timing diagram of clock signals in the gating circuit of FIG. 4.

In the dual clock circuit 30, a 32 kHz crystal oscillator 32 is counted down to 2 kHz by counter 34. The 2 kHz signal and its complement 2 kHz-bar are gated in logic circuits 36 and 38 by 32 kHz as shown in FIGS. 4 and 5 to create the outputs "gated 2 kHz" and "gated 2 kHz-bar". These two clock outputs are complementary except that the rise of each clock pulse is delayed 15.6 microseconds to ensure break-before-make action as shown in FIG. 5.

While $T_V$-bar and $T_A$-bar are high (sensing mode) gates 26 and 28 cooperate to reproduce the gated 2 kHz output of clock circuit 30 of FIG. 4, as shown in FIG. 6. Likewise, the gated 2 Khz-bar clock signal is passed via gates 40 and 42 of FIG. 4. Consequently, the atrial and ventricular gates are complementary, except for the "break" time.

When a ventricular stimulation pulse occurs, $T_V$-bar goes low and causes the atrial gate to go low and the ventricular gate to go high so that the ventricular output pulse is passed only to electrodes V1 and V2 in FIG. 3. When C6 becomes sufficiently discharged through R8, $T_V$-bar goes high. Conversely, when $T_A$-bar goes low for an atrial stimulation, the atrial gate goes high and the ventricular gate goes low. After the stimulation pulse, the complementary 2 kHz gating resumes, as shown in FIG. 6.

All of the logic components are CMOS powered by $V_{dd}$. Characteristic component values and identities are given in the following table only by way of illustration for the specific embodiment of FIGS. 3 and 4.

TABLE

| R1 | 27 kilohms | C4 | 22 microfarads |
|---|---|---|---|
| R2 | 27 kilohms | C5 | 0.01 microfarad |
| R3 | 10 megohms | C6 | 0.01 microfarad |
| R4 | 10 megohms | C7 | 10 picofarads |
| R5 | 10 megohms | C8 | 56 picofarads |
| R6 | 10 megohms | C9 | 0.01 microfarad |
| R7 | 100 kilohms | C10 | 0.01 microfarad |
| R8 | 1.5 megohms | C11 | 0.01 microfarad |
| R9 | 10 megohms | Counter 34 | CD 4020 |
| R10 | 100 kilohms | Quad analog switch 18 Intersil IH 5145 | |
| R11 | 1.5 megohms | CR1, CR2 | 1N9474 |
| C1 | 22 microfarads | Q1, Q2 | 2N5210 |
| C2 | 22 microfarads | $V_{dd}$ | +5V logic level |
| C3 | 22 microfarads | +V | +27V output level |

The multiplexing system described above creates effective interchannel separation allowing the use of two bipolar leads with the same ground terminal. Thus in implanted pacers there is no need to use space-consuming separate power supplies for the channels or bulky transformers to accomplish channel separation.

Moreover, the system does not interfere with existing pacer circuitry and can therefore be designed as an add-on circuit. This multiplexing system is particularly well suited to external pacing systems. The ability to detect cardiac signals is not impaired since the clock or sampling frequency of 2 kHz is more than ten times the highest frequency component in the intra-cardiac waveform and sense amplifier bandpass. In any event the period of the sampling frequency should be substantially less than the P-wave duration.

Variations on the configuration and detailed implementation of the foregoing system can be made without departing from th principle and spirit of the invention, the true scope of which is indicated by the following claims and equivalents thereto.

What is claimed is:

1. A dual channel cardiac pacing system of the type comprising a three terminal cardiac pacer pulse generator and two bipolar leads, wherein the improvement comprises multiplexor means connected between the leads and the pulse generator for isolating said leads and further including means for alternately connecting said leads to said pulse generator for equal intervals of time at a predetermined fixed rate, having a period less than the P-wave duration and independent of the stimulation rate.

2. The system of claim 1 wherein said predetermined rate is above 1 kHz.

3. The system of claim 1 wherein said predetermined rate is on the order of 1 kHz.

4. The sytem of claim 1 wherein said predetermined rate is 2 kHz.

5. The system of claim 1 wherein said multiplexor means further includes means responsive to a pulse generator output for immediately connecting the corresponding lead and disconnecting the other lead for a predetermined time interval, whereby the stimulation pulse is applied exclusively via the respective bipolar lead.

6. The system of claim 1, wherein said multiplexor means further includes analog switch means for multiplexing said leads having a first pair of switches for one lead and a second pair of switches for the other lead responsive to respective substantially complementary gating signals, and means for producing said gating signals at a predetermined rate with a period less than the P-wave duration.

7. The system of claim 6, wherein said gating signal producing means includes means for responding to said pulse generator output for temporarily holding said gating signals in the corresponding complementary conditions longer than said pulse generator output.

8. The system of claim 7, wherein said holding means includes means for holding the condition of said gating signals for a fixed interval irrespective of the duration of said pulse generator output.

9. The system of claim 8, wherein said gating signal producing means includes means for producing a pair of clock signals which are complementary except that the rising edge of each is delayed by a predetermined fraction of the clock period, a pair of one-shot means connected to be triggered by the respective pulse generator outputs for producing respective pulse outputs and a pair of logic means responsive to the outputs of both one-shot means and the respective clock signals for producing respective complementary gating signals at the clock signal frequency except for a predetermined interval covering a pulse generator output during which the gating signals assume a corresponding constant condition.

* * * * *